United States Patent [19]
Ginsberg et al.

[11] 3,932,065
[45] Jan. 13, 1976

[54] PNEUMATICALLY CONTROLLED LIQUID TRANSFER SYSTEM

[75] Inventors: Guenter Ginsberg, Miami; Thomas John Godin, Hollywood; Ronald Olin Simpson, Miami, all of Fla.

[73] Assignee: Coulter Electronics, Inc., Hialeah, Fla.

[22] Filed: Nov. 8, 1974

[21] Appl. No.: 522,012

Related U.S. Application Data

[62] Division of Ser. No. 382,741, July 26, 1973, Pat. No. 3,882,899.

[52] U.S. Cl. ............... 417/317; 137/627.5; 251/5; 251/7; 417/384; 417/388; 417/393; 417/399
[51] Int. Cl.² .... F04B 9/00; F04B 9/12; F04B 17/00
[58] Field of Search ........... 417/149, 384, 388, 389, 417/479, 317, 392, 393, 399, 401; 128/214 B; 251/5, 7; 137/627.5

[56] References Cited
UNITED STATES PATENTS

| | | | |
|---|---|---|---|
| 1,072,718 | 9/1913 | Heindl | 417/399 |
| 2,471,623 | 5/1949 | Hubbell | 251/7 X |
| 2,985,192 | 5/1961 | Taylor et al. | 251/7 |
| 3,543,752 | 12/1970 | Hesse et al. | 128/214 E |

*Primary Examiner*—C. J. Husar
*Assistant Examiner*—Richard E. Gluck
*Attorney, Agent, or Firm*—Silverman & Cass, Ltd.

[57] ABSTRACT

A pneumatically controlled liquid transfer system for delivering a liquid from a source to a delivery location, said liquid source being provided with a pneumatic cylinder for driving the liquid from said source, a pneumatically operated pinch valve of the make-before-break type and flexible conduit paths leading through the valve to the delivery location. The make-before-break pinch valve comprises a valve shell having two pistons movable laterally therein. The shell has a window. One piston has a yoke, each arm thereof having a passageway, one aligned with the other. A stop extends between the arms of the yoke. One of the flexible conduits is arranged through the window between the first piston and the yoke and the other flexible conduit is arranged also through the window but within the aligned passageways and between the piston and post. The second piston is spring biased to bear against the second conduit to place same in a normally closed condition. The first conduit is normally open. The first piston is acted upon by an external force such as air pressure to move same to a first condition wherein the piston pinches the first flexible conduit against the yoke, closing said conduit without overcoming the bias of the second piston to open the second conduit. Continued force exercised upon said first piston causes the same to move laterally within the housing to a second condition overcoming the spring bias of the second piston, to open the second conduit while the first conduit is retained in closed position. The second piston by virtue of its spring bias, will force the yoke back into its first position once the pressure on the first piston is laxed. A manual override is provided operative upon the second piston to lock the same in open condition so that both conduits are open. This last mentioned position is utilized during down time of the apparatus concerned.

10 Claims, 6 Drawing Figures

PNEUMATICALLY CONTROLLED LIQUID TRANSFER SYSTEM

This is a Division, of application Ser. No. 382,741 filed July 26, 1973, now U.S. Pat. No. 3,882,899.

BACKGROUND OF THE INVENTION

This invention relates generally to apparatus for automated chemical analysis and more particularly concerns the provision of a pneumatically controlled liquid transfer system particularly useful with such apparatus.

It will be appreciated that apparatus intended automatically to make a plurality of chemical tests upon a series of individual samples which are fed to said apparatus generally is known in the art. Such automated chemical analysis apparatus is utilized for example in the medical field, for diagnostic and routine informational purposes, and often for research. Chemical tests are performed on a series of individual samples. Often physical tests are performed additionally on these samples. Classically, all such tests were performed manually, by trained technicians in laboratories. In a typical chemical test in the medical field, for example, a sample of blood would be drawn from a patient, spun in a centrifuge to separate the plasma from the cells with the plasma decanted and placed in a container identified as to the patient. A small quantity of plasma would be measured into a reaction tube, mixed with a proper proportion of some chemical reagent, and maintained for a precise time at a precisely maintained temperature. Thus a certain chemical reaction would be permitted which will change the color of the mixture, providing a quantitative indication, say of the concentration in the plasma of the particular agent sought in the test being performed. The reaction tube would then be decanted into a cuvette, and a beam of light of predetermined wavelength directed through the cuvette, and, perhaps absorbance measured.

Over a period of years, these chemical tests have been developed to a relatively high degree of acceptance to ascertain such information as for example, the total protein of the blood, the presence of certain chemicals such as phosphorous, potassium, sodium and calcium; the amount of creatinine in the blood; the amounts of different enzymes, albumen, etc. Laboratories may perform as little as one or two tests on an available sample, or as many as twenty. The reagent composition, the proportions, the incubation time and temperature, etc. vary from test to test, but must be carefully monitored so that the results may comply with the requirements for precision and accuracy. Problems are inherent in the manual execution of these tests by a technician and hence, desired obviation of these problems have given rise to automated or at least semi-automated chemistry testing apparatus.

Among the problems associated with manual performance of the test concerned are the likelihood of human errors promoted by the measurements which must be made manually, the need for entering information and data relating to the sample and keeping its identification straight, tediousness and fatigue of the technician, errors in choosing the proper chemicals and using the proper proportions and the failure to keep the equipment clean of contamination. Loss of time, expense, waste, etc. are some other disadvantages encountered in performance of the classical analytical methods.

The art then has provided many different types of apparatus to perform automatic chemical analysis but resolving the problems inherent in varying degree with the classical analytical methods. Among structures utilized for this purpose, include those where turntables are employed which rotate to a sample withdrawing position. Samples are withdrawn thereat, diluted and passed to the processing portion of the apparatus. One form of apparatus involves the diluted samples passing through conduits one after the other separated by quantities of diluent and bubbles. In other systems, the diluted samples are carried in reaction tubes placed on continuous drums or conveyors.

One particular problem encountered in known automated chemical analysis apparatus involves the efficiency of transfer of liquids in such a manner as to provide quantitatively accurate dilutions and satisfactory physical transfer of the diluted test samples to the container within which they are incubated and later analyzed by way of optical or other methods. Transfer of such liquid materials is a serious problem in achieving precision and accuracy.

One persistant problem encountered involves the necessity to switch from one fluid source to another. Fluid valves, commonly known as check valves, are used to control the direction of fluid flow. Check valves are intended to allow fluid flow therethrough in one direction.

Generally, an apparatus utilizing check valves comprises a cylinder chamber with its associated cylinder head for changing the pressure within the chamber. The cylinder chamber has a pair of ports to which are coupled a pair of check valves having the direction of fluid flow respectively oppositely oriented. When the cylinder head is stroked to cause an increase in the cylinder chamber's volume, fluid is drawn into the chamber with the opening of the first valve and closing of the second.

The piston on the cylinder is stroked to decrease the cylinder chamber's volume whereby the fluid therein is discharged by way of the now opened second valve by way of the first valve being in closed position. Accurate volume measurements are required when quantities of liquid reactants can be transferred say from a source to a test tube or reaction tube for subsequent analysis. In some apparatus there are devices for drawing a precisely known quantity of first liquid, let us say sample by way of example, into a chamber, subsequently washing said chamber with a known quantity of diluent transferred thereto from a source thereof and thereby discharging the precisely diluted mixture to a delivery location.

The above described systems depend on check valves in the liquid conduits. These are quite often the least reliable elements of the system as a whole. Many check valves are subject to sealing or seating problems, which may be caused by sedimentary buildup formed upon the sealing mechanism and thereby introducing error due to the extra fluid that would leak through the valve when the proper sealing has not occurred. Other problems associated with the many prior valves involve the mechanical hysterisis or "backlash" that occurs due to the time delay between the time the pressure is changed to close the valve and the time that the valve actually closes. This "backlash" allows additional fluid to pass — thereby to be dispensed, causing additional error in the volume measurement. It also has been found that "backlash" error is generally unpredictable because such error is a function of the back pressure applied to the valve to cause the valve to close. The back pressure is usually a variable in any pumping system and may be unpredictable.

Many prior art valves were subject to sealing or seating problems caused by swelling of the sealing parts of the valve so that the valve does not properly close or seal. Further, prior art valves of the character concerned are not interchangeably capable of handling corrosive fluids without utilizing special constructional material.

Other advantages will be evident in the course of the description of a preferred embodiment of the liquid transfer system and the particular valve therefor provided by the invention.

SUMMARY OF THE INVENTION

A pneumatically controlled liquid transfer system comprising first and second chambers and first and second pneumatic drive means associated with said first and second chambers respectively, first and second flexible conduit paths leading respectively from said chambers to a delivery location and pinch valve means interposed in said conduit paths for controlling flow therein.

The pinch valve means of the invention comprise a valve shell having a window and a pair of pistons mounted for lateral movement within the shell selectively to open and close flexible conduits passed through the valve. One of the pistons has a yoke and the shell is provided with a stop transverse the yoke in a direction normal to the path of the flexible conduits. The first flexible conduit is passed between the first piston and the yoke, and the second flexible conduit is passed between the post and the second piston. The yoked piston is spring biased normally to close the second conduit by pinching same. Means are provided which are capable of exerting force upon the first piston to effect lateral movement thereof. The first piston thus is acted upon to move to a position pinching the first flexible tube against the yoke. The second tube is maintained in closed condition and the first tube is urged by said first piston against the yoke placing both conduits in closed condition. The first piston is urged further in a lateral direction toward the yoke to move same to a second condition opening the second conduit while the first conduit remains closed. The pressure on the first piston is relaxed. The yoke is spring biased to return to its first position during the return of the first piston to its first position, thereby opening the first conduit and closing the second. Means are coupled to the second piston manually to override the spring bias thereof whereby the second conduit as well as the first can be maintained in open condition during down time of valve. In this way, the elastomeric memory of the flexible conduit which would tend to cause the pinched conduit to remain closed after some prolonged period of forced closing even when the force is removed, is obviated.

DESCRIPTION OF PREFERRED EMBODIMENTS

In order to understand the advantages offered by the liquid transfer system in accordance with the invention, it will be helpful to review briefly a typical liquid transfer system utilized in the prior art and particularly in automated chemical testing apparatus.

The desire is to transport predetermined precisely measured quantity of liquid sample to a delivery location. On some occasions the sample is mixed and diluted in the course of such transfer. At times it is even mixed with a reagent in precise measured quantities during the course of such transfer.

In the prior art expedients such as the use of check valves to assure one way movement of the respective liquids in the conduit means provided have been successfully utilized. However, such check valves suffer from inherent problems such as inability to resist, for any length of time, the often corrosive liquids to which they are directly exposed. Likewise, sedimentary build-up on the sealing elements, swelling, inability to properly seal and a certain lag time in actual operation, as has been explained, result in such prior expedients not being as reliable as is desired in such automatic testing equipment.

For example, a syringe like container may be provided in which there is a piston reciprocably operated say be programmed electrically operated drive means. The measuring chamber of the cylinder is connected by way of a check valve to a source of sample liquid with the check valve operable only to permit feeding of sample liquid to the chamber. The second conduit, perhaps the discharge conduit, is coupled by way of a second check valve to a delivery location, let us say a test tube. The second check valve is operable to permit flow only in the discharge direction to the delivery location. When the piston, within its syringe-like cylinder, is raised sample liquid is drawn past the first check valve into the chamber. When the syringe piston is moved to compress or reduce the volume within the chamber, the liquid therein passes only through the second conduit past the second check valve to the delivery location. This is a simple form of liquid transfer.

A slightly more complex arrangement involves the use of three check valves, one operable to pass sample liquid into a chamber, a second operable to pass diluent into the same chamber, and the third operable to pass the resulting mixture from the chamber to a delivery location.

Figure 1:
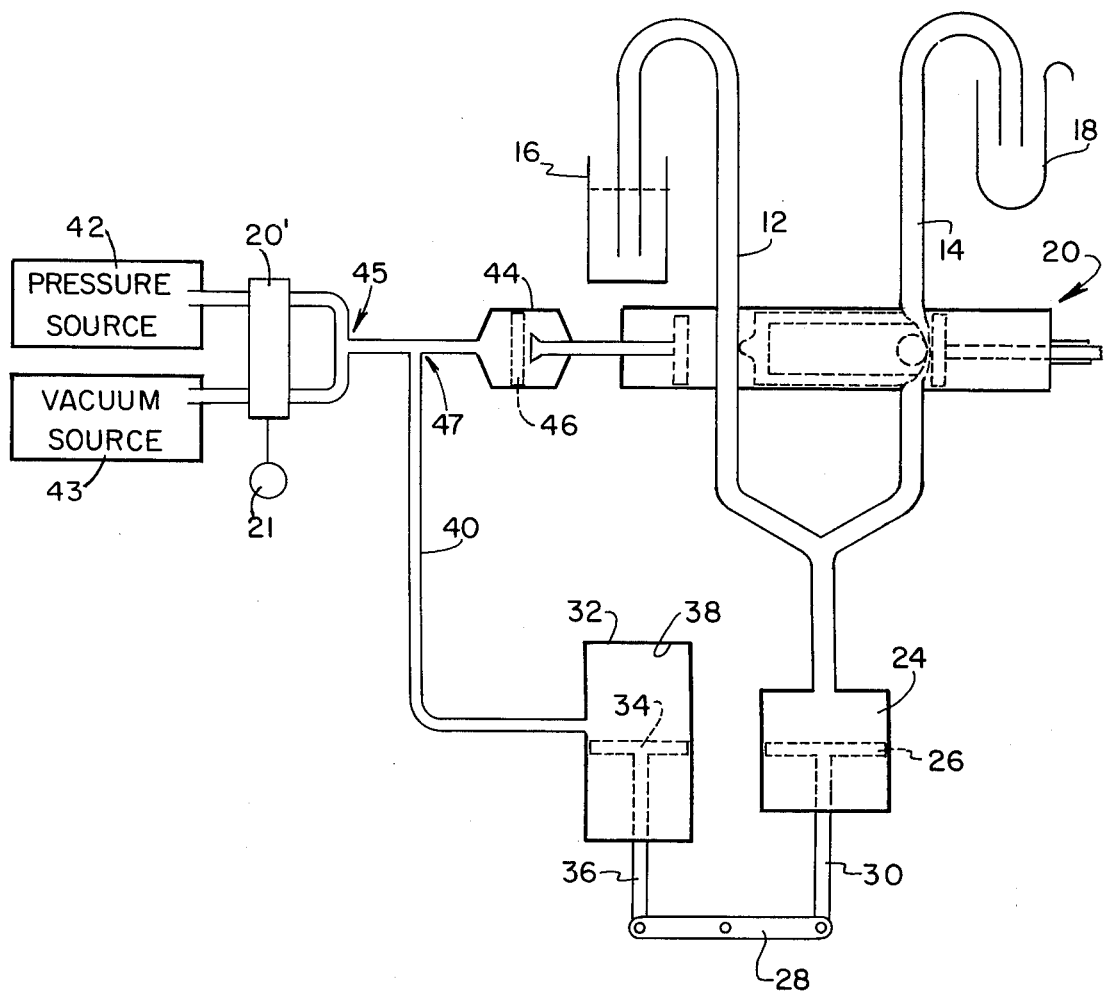
FIG. 1 is a schematic representation of the pneumatically controlled liquid transfer system according to the invention.

With the above in mind, a reference is made to FIG. 1 where a liquid transfer system constructed in accordance with the invention is schematically represented. A pair of flexible tubes 12 and 14 are coupled respectively to a source of sample 16 and to a delivery location 18. Such conduits 12 and 14 are passed through a single pinch valve 20 to a "Y" connection and thence into the chamber of cylinder 24. Cylinder 24 carries a reciprocable piston 26 operated by a linkage 28 connected to plunger 30 of piston 26. A second cylinder 32 carrying a reciprocal piston 34 is coupled by way of plunger 36 to the linkage 28. Thus, the cylinder 32 operates to control the operation of the piston 26 of cylinder 24. The chamber 38 of cylinder 32 is coupled by way of conduit 40 to a source of compressed air 42. Air also is supplied to cylinder 44 from source 42 to operate piston 46 operating the pinch valve 20.

Normally the pinch valve 20 is arranged so that tube 12 is open while tube 14 is closed. When air is supplied from source 42 to the cylinder 44, the valve 20 is operated to close the tube 12 with tube 14 remaining closed. Continued application of air from source 42 to the cylinder 44 thereafter will cause the conduit tube 14 to be opened while tube 12 remains closed.

Simultaneously air is introduced into the chamber 38 of cylinder 32 by way of conduit 40 driving the piston 34 down and forcing piston 26 upward in cylinder 24 to compress the chamber within said cylinder 24, expelling any liquid to the delivery location 18 by way of tube 14, now opened. Application of suction by way of tube 40 to the chamber 38 causes the piston 34 to be raised thereby lowering the piston 26 and creating a suction within the chamber of cylinder 24. Such relaxation or release from cylinder 44 likewise causes the pinch valve to reverse its operation, closing tube 14 and thereafter opening tube 12. Now, a sample liquid will be sucked through tube 12 from source 16 into the chamber of cylinder 24. A pinch valve 20' controlled by actuator 21 is shown interposed as a switch to enable alternating application of air pressure from source 42 and vacuum from source 43 to cylinders 32 and 44 by way of T-connections 45 and 47 respectively.

Thus it is noted that the fluids transferred never contact the valve as would be the case of check valves, and since the valve 20 is of a make-before-break variety, there is assurance of swift cutoff in the operation of the valve 20.

Figure 2:
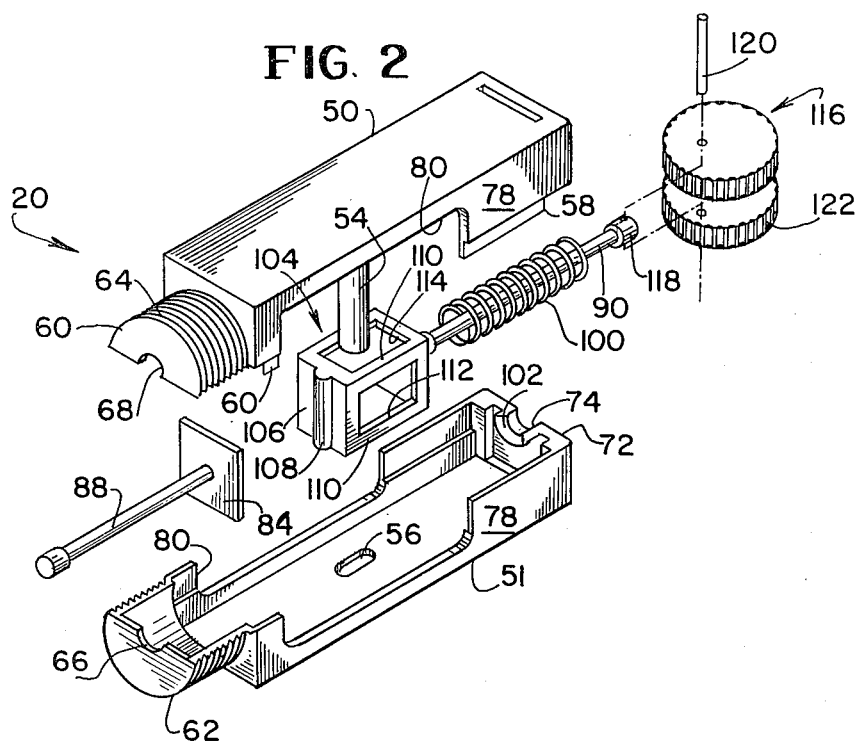
FIG. 2 is an exploded view of the pinch valve constructed in accordance with the invention.

Reference is made to FIG. 2 for a description of the construction of the pinch valve 20. In FIG. 2 the valve 20 is illustrated in exploded perspective view and is shown in assembled condition in FIG. 3 in its so-called normal condition.

The pinch valve 20 according to the invention comprises a housing formed as an assembly of a pair of half shells 50 and 52 preferably molded of plastic material. Shell 50 has an integral post 54 which is capable of being received tightly in an opening 56 of conforming configuration. Suitable tabs 58 and 60 are provided to facilitate the force fitted assembly of the shells 50 and 52. Each of the half shells 50 and 52 has semi-cylindrical portions 60 and 62 each having threaded outer surfaces 64. Semicircular notches 66 are provided in each of the semicylindrical portions 60 and 62 so that when assembled, portions 60 and 62 define a cylindrical threaded nipple 68 having an axial passage 70. The end walls 72 of shells 50 and 52 likewise have semicircular notches 74 which define, when assembled, an axial passage 76. The side walls 78 of the shells 50 and 52 have elongate laterally extending notches 80 formed therein so as to define a window 82 in the side walls of the assembled housing. A pair of pistons 84 and 86 having plungers 88 and 90 are seated respectively within the assembled housing. Plunger 88 is reciprocable through passage 70 while plunger 90 is reciprocable through passage 76.

A helical coil spring 100 is arranged on plunger 90 with a suitable seat therefor defined, on assembly of the shells 50 and 52, by inwardly directed semi-cylindrical protrusions 102 formed on end walls 72 at a location adjacent the notches 74. The piston 86 includes a yoke-like formation 104. The formation 104 is defined by plate 106 carrying outer rib 108 and connected to the piston 86 by corner posts 110. The posts 110 define windows 112 and 114. Windows 112 are aligned with the windows 82 of the housing while the post 54 passes through window 114.

Figure 6:
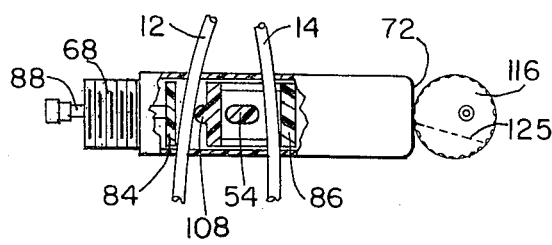
FIG. 6 is a view similar to that of FIG. 4 but illustrating the pinch valve in its down time condition.

An eccentric wheel 116 is secured axially to free end 118 of plunger 90 by pin 120. The wheel 116 comprises a pair of spaced aligned cylindrical members having knurled circumferential surfaces 122 and circumferential integral connecting portion 124 having a planar or flat inner surface 125. When the wheel 116 is rotated, the plunger 90 is moved laterally with the lateral movement of the pin 120 to a condition where it is locked, as shown in FIG. 6, by engagement with flat 125. The wheel 116 bears against the end of the housing adjacent thereto due to the spring 100 and operates in the manner of cam means.

Figure 3:
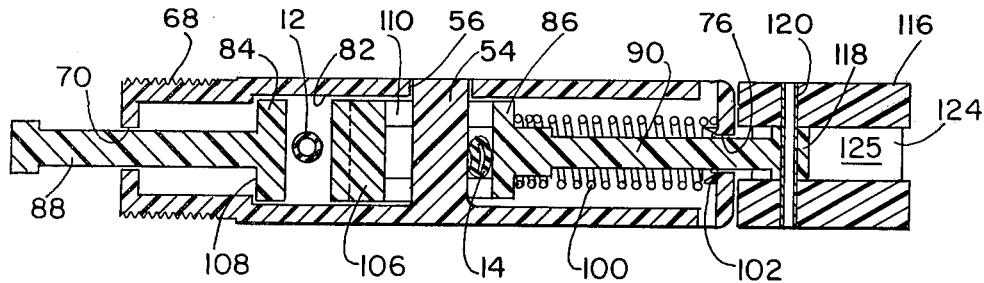
FIG. 3 is a sectional view of the pinch valve constructed in accordance with the invention and illustrated in its normal condition.

In FIG. 3 the pinch valve 20 is illustrated in its normally assumed operating condition with the tubes 12 and 14 threaded through the windows 82. The tube 12 passes between the piston 84 and the rib 108 of yoke 92. The tube 14 is threaded through windows 82 between the post 54 and the piston 86. Normally, the piston 86 is biased by spring 100 to pinch the tube 14 closed.

Figure 4:
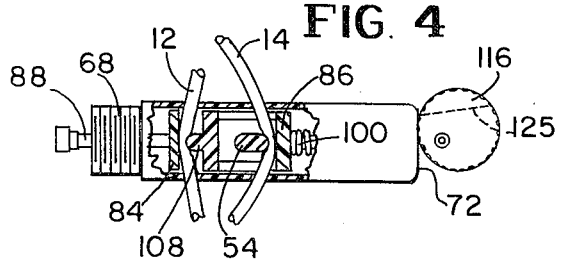
FIG. 4 is a reduced side view of the pinch valve according to the invention illustrated in a first condition of operation, with portions broken away and shown in section to show interior detail.
Figure 5:
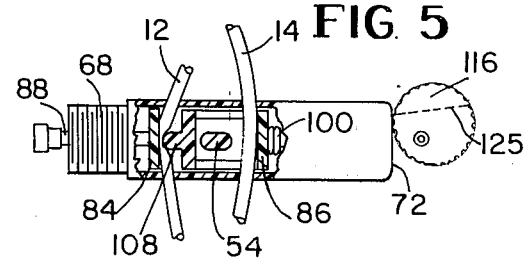
FIG. 5 is a view similar to that of FIG. 4 but illustrating another stage in the operation of the valve.

Application of force to the plunger 88 and thereby to piston 84 moves the piston 84 laterally to compress the tube 12 against the rib 108, closing the tube 12. This condition is illustrated in FIG. 4, where both tubes 12 and 14 are pinched closed. Continued application of force to the plunger 88 drives the piston 84 forcing the yoke formation 104 laterally to the right, as illustrated in FIG. 5, to overcome the bias of the spring 100 opening normally closed tube 14 while the tube 12 remains in closed condition. Relaxation of the force applied to piston 88 causes the yoke formation 104 to return, same moving laterally to the left. Again both tubes 12 and 14 are closed before tube 12 is reopened.

The eccentric wheel 116 is rotated manually to override the normal bias of the spring 100 and move the piston 90 laterally to the right, opening the tube 14. The piston 90 is held at the condition until the wheel 116 is rotated in the opposite direction. The elastomeric tubes inherently have a structural memory. If such tubes are maintained in a closed or pinched condition for some length of time, the elastomeric memory thereof to open condition can be lost, with the tube remaining pinched notwithstanding release of the spring bias causing the pinched condition. Thus, the eccentric wheel 116 is rotatable to move the piston 80 to a position spaced from the post 54 and to retain that position. This expedient is utilized when the apparatus concerned is shut down, for example overnight. When operation is desired, the eccentric wheel 116 is rotated in the opposite direction releasing piston 90 and placing the valve in normal operational condition.

It is desirable that the valve 20 is made of plastic material and that the tubes 12 and 14 are formed of a suitable elastomeric material such as, for example, an elastomeric silicone rubber or a fluoraelastomer marked by E. I. DuPont DeNemours & Co. under the trademark VITON.

Any suitable actuator means can be utilized to apply selectively force to the plunger 88 to drive the piston 84, and operate the pinch valve 20. Preferably pneumatically operated piston means utilizing a source of alternately applied compressed air and vacuum has been effectively utilized. The valve 20 also can be utilized as switch means controlling application of vacuum and pressure to the air cylinder 32, for sample, and even to the piston 84, as represented by valve 20' in FIG. 1.

What it is desired to be secured by letters Patent of the United States is:

1. A pneumatically controlled liquid transfer system comprising a source of vacuum and pressure, first and second chambers, each chamber having a port, a tube connecting the source of vacuum and pressure to the port of one of said chambers, first and second flexible conduit paths coupled to a delivery location and a source of liquid respectively, said first and second flexible conduit paths connected to the port of the other of said chambers, a make-before-break pinch valve including actuating means therefor interposed in said respective flexible conduit paths for sequentially controlling liquid flow in said paths, the drive means of said one chamber being driven by said source of vacuum and pressure and driving the drive means in said other chamber, the drive means in said other chamber drawing liquid into said other chamber from said source of liquid and further delivering said liquid to said delivery location, and means coupling said vacuum and pressure source to said actuating means for said pinch valve for operation thereof, said pinch valve comprising a pair of pistons sequentially operable within a housing, said pair of flexible conduit paths being disposed respectively in the path of said pistons, one of said conduit paths being normally opened and the other of said conduit paths being normally closed, said actuating means causing one of said pistons to move in a first direction, and means biasing the other of said pistons in a second direction opposed to the first direction, pressure being applied from said source of vacuum and pressure to said actuating means driving said one piston in said first direction whereby to close the open one of said conduit paths while maintaining the other of said conduit paths in its normally closed condition, thereafter further to move said one piston in said first direction overcoming the bias of said other piston to open said normally closed other of said conduit paths.

2. The system as claimed in claim 1 in which said drive means comprises a piston reciprocably movable within each respective chamber.

3. The system as claimed in claim 1 in which said chambers are cylindrical and said drive means comprises a piston reciprocable within each respective chamber.

4. The system as claimed in claim 1 in which there is a pivotal coupling linkage between said drive means.

5. The system as claimed in claim 1 in which said source of vacuum and pressure constitute separate sources and second pinch valve means interposed between said separate sources and both of said one chamber and said actuating means.

6. A pneumatically controlled liquid transfer system comprising a source of vacuum and pressure, first and second chambers, each chamber having a port, a tube connecting the source of vacuum and pressure to the port of one of said chambers, first and second pneumatically operated drive means associated with said first and second chambers respectively, first and second flexible conduit paths coupled to a delivery location and a source of liquid respectively, said first and second flexible conduit paths connected to the port of the other of said chambers, a make-before-break pinch valve including actuating means therefor interposed in said respective flexible conduit paths for sequentially controlling liquid flow in said paths, the drive means of said one chamber being driven by said source of vacuum and pressure and driving the drive means in said other chamber, the drive means in said other chamber drawing liquid into said other chamber from said source of liquid and further delivering said liquid to said delivery location, and means coupling said vacuum and pressure source to said actuating means for said pinch valve for operation thereof, said pinch valve comprising a pair of pistons sequentially operable within a housing, said pair of flexible conduit paths being disposed respectively in the path of said pistons, one of said conduit paths being normally opened and the other of said conduit paths being normally closed, said actuating means moving in a first direction causing one of said pistons to move in a first direction, and means biasing the other of said pistons in a second direction opposed to the first direction, pressure being applied from said source of vacuum and pressure to said actuating means driving said one piston in said first direction whereby to close the open one of said conduit paths while maintaining the other of said conduit paths in its normally closed condition, thereafter further to move said actuating means in said first direction counteracting the bias on said other piston to open said normally closed other of said conduit paths.

7. The system as claimed in claim 6 in which said drive means comprises a piston reciprocably movable within each respective chamber.

8. The system as claimed in claim 6 in which said chambers are cylindrical and said drive means comprises a piston reciprocable within each respective chamber.

9. The system as claimed in claim 6 in which said source of vacuum and pressure constitute separate sources and a second make-before-break pinch valve interposed between said separate sources and both of said one chamber and said actuating means.

10. A pneumatically controlled liquid transfer system comprising a source of vacuum and pressure, a cylinder including a port and a plunger reciprocable within said cylinder, first and second flexible conduit paths connected to said port and communicatively coupling said port to a source of liquid and to a delivery location respectively, means operably connected to said source of vacuum and pressure for drivingly reciprocating said plunger within said cylinder alternately for drawing of liquid from said source to said cylinder and delivery of liquid to said delivery location, a make-before-break pinch valve including actuating means therefor, interposed in both said flexible conduit paths for sequentially controlling liquid flow in said paths, means coupling said source of vacuum and pressure to said actuating means for said pinch valve for operation thereof, said pinch valve comprising a pair of pistons sequentially operable within a housing, said pair of flexible conduit paths being disposed respectively in the path of said pistons, one of said conduit paths being normally opened and the other of said conduit paths being normally closed, said actuating means moving in a first direction causing one of said pistons to move in a first direction, and means biasing the other of said pistons in a second direction opposed to the first direction, pressure being applied from said source of vacuum and pressure to said actuating means driving said one piston in said first direction whereby to close the open one of said conduit paths while maintaining the other of said conduit paths in its normally closed condition, thereafter further to move said actuating means in said first direction counteracting the bias on said other piston to open said normally closed other of said conduit paths.

* * * * *

UNITED STATES PATENT AND TRADEMARK OFFICE
CERTIFICATE OF CORRECTION

PATENT NO. : 3,932,065
DATED : January 13, 1976
INVENTOR(S) : Guenter Ginsberg, et al It is certified that error appears in the above-identified patent and that said Letters Patent are hereby corrected as shown below:

In column 6, line 48, change "the" to read "that".

In column 7, line 17, after "chambers" the following should be inserted, --first and second pneumatically operated drive means associated with said first and second chambers respectively--.

In column 8, line 26, after the word "source" delete the comma (,).

Signed and Sealed this

First Day of February 1977

[SEAL]

Attest:

RUTH C. MASON
Attesting Officer

C. MARSHALL DANN
Commissioner of Patents and Trademarks